(12) United States Patent
Roscoe et al.

(10) Patent No.: US 7,635,452 B2
(45) Date of Patent: Dec. 22, 2009

(54) SYSTEM, KIT, AND METHOD FOR MEASURING MEMBRANE DIFFUSION

(75) Inventors: Stephen B. Roscoe, St. Paul, MN (US); Neal A. Rakow, Woodbury, MN (US); Michael L. Husberg, West St. Paul, MN (US); Lester H. McIntosh, III, Green Lane, PA (US)

(73) Assignee: 3M Innovative Properties Company, St. Paul, MN (US)

( * ) Notice: Subject to any disclaimer, the term of this patent is extended or adjusted under 35 U.S.C. 154(b) by 1185 days.

(21) Appl. No.: 10/669,276

(22) Filed: Sep. 24, 2003

(65) Prior Publication Data

US 2005/0063862 A1   Mar. 24, 2005

(51) Int. Cl.
   *G01N 33/00* (2006.01)
(52) U.S. Cl. ............... 422/68.1; 422/81; 422/50
(58) Field of Classification Search ............... 422/68.1, 422/81, 50
   See application file for complete search history.

(56) References Cited

U.S. PATENT DOCUMENTS

| 4,511,534 | A | * | 4/1985 | Bennett et al. ............... 422/100 |
| 5,490,415 | A | | 2/1996 | Mak et al. |
| 5,591,636 | A | * | 1/1997 | Grass ............... 435/287.1 |
| 6,043,027 | A | | 3/2000 | Selick et al. |
| 6,439,036 | B1 | | 8/2002 | Mansky |
| 6,455,007 | B1 | | 9/2002 | Mansky et al. |
| 6,521,191 | B1 | | 2/2003 | Schenk et al. |
| 6,662,635 | B2 | | 12/2003 | Mansky |
| 2002/0025509 | A1 | | 2/2002 | Cima et al. |

FOREIGN PATENT DOCUMENTS

WO    WO 02/16941 A2    2/2002

OTHER PUBLICATIONS

U.S. Appl. No. 10/669,390, filed Sep. 24, 2003, Method of Formulating a Pharmaceutical Composition.
Houk et al., "Membrane Models for Skin Penetration Studies", Chemical Reviews, vol. 88(3), pp. 455-472 (1988).
Hatanaka et al., "Prediction of Skin Permeability of Drugs. II. Development of Composite Membrane as a Skin Alternative", International Journal of Pharmaceutics, vol. 79, pp. 21-28 (1992).
Franz, "Systems for Percutaneous Absorption of Pharmaceutical Compounds, Cosmetics and Toxic Substances", Crown Glass Company, Inc., (Date Unknown) pp. 2-16.
"Permeation Test Cell ASTM F-739, F-1383", A.A. Pesce Glass Company, [retrieved from the internet on Jul. 21, 2003], www.pesceglass.com/ptc.asp, pp. 2.
Laboratory Glass Apparatus, Inc., [retrieved from the internet on Jul. 21, 2003], www.laboratoryglassapparatus.com, pp. 13.

* cited by examiner

*Primary Examiner*—Sam P Siefke
(74) *Attorney, Agent, or Firm*—Bradford B. Wright

(57) ABSTRACT

A system for measuring diffusion of a compound across a membrane generally comprises a membrane held between a first base having a plurality of outwardly extending hollow projections and a second base fastened to the first base and having a plurality of recessed tapered openings therein adapted to engage the plurality of hollow projections. Methods for measuring membrane diffusion using such systems are included. The system components are also provided in kit form.

22 Claims, 4 Drawing Sheets

SYSTEM, KIT, AND METHOD FOR MEASURING MEMBRANE DIFFUSION

BACKGROUND

The development of transdermally deliverable pharmaceutical compositions typically involves a screening and refinement process in which a large number of pharmaceutical compositions are evaluated. Typically the compositions include one or more pharmaceuticals and one or more compounds (commonly known as excipients or enhancers) that increase diffusion of the pharmaceutical(s) across the membrane of interest (e.g., skin). Hundreds of useful excipients are known, and the specific choice of excipients for a given pharmaceutical typically involves an extensive screening process involving many membrane diffusion measurements.

Typical systems for measuring membrane diffusion have two chambers separated by a membrane (e.g., skin). Typically, one chamber contains a pharmaceutical composition to be tested (e.g., as a solution or in a transdermal patch), and the other chamber contains a recipient solution representative of serum. The pharmaceutical composition and the recipient solution each contact opposite surfaces of the membrane. The concentration of the pharmaceutical in the receiving solution is periodically measured and the diffusion rate of the pharmaceutical across the membrane determined. In order to obtain accurate membrane diffusion measurements, it is typically important that air gaps between the pharmaceutical composition, the receiving solution, and the membrane be avoided.

Widely used commercially available systems of the two-chamber type include Ussing chambers, Franz cells, in-line cells, and horizontal cells. Many such devices are only capable of making individual measurements and/or require relatively large areas of membrane to operate.

Systems that can perform multiple diffusion measurements in parallel using a single membrane have been reported. In essence, such systems divide the membrane into a plurality of separate regions, each of which serves as a membrane of a distinct two-chamber type cell. In such systems, it is generally important that the cells remain effectively isolated from each other (i.e., contents of one cell cannot enter into another cell).

There remains a need in the art for systems and methods that are useful for rapidly screening large numbers of formulations while efficiently using the membrane material.

SUMMARY

In one aspect, the present invention provides a system for measuring diffusion of a compound across a membrane comprising:

a first base having first and second opposed surfaces and having a plurality of hollow projections extending outwardly from the first surface, each hollow projection having a tapered tip with an opening therein and a respective cavity contiguous with the opening disposed within the projection;

a second base having first and second opposed surfaces, the first surface having a plurality of recessed tapered openings therein adapted to engage the plurality of hollow projections, each recessed tapered opening being contiguous with a respective cavity that extends into the second base; and a membrane contacting the recessed tapered openings and the tips of the hollow projections, wherein the first base is fastened to the second base by a first fastening means, and wherein: a) each cavity within a hollow projection extends through the first base and forms an opening at the second surface of the first base; or b) each cavity within the second base extends through the second base and forms an opening at the second surface of the second base; or c) each cavity within a hollow projection extends through the first base and forms an opening at the second surface of the first base, and each cavity within the second base extends through the second base and forms an opening at the second surface of the second base.

In some embodiments, the system further comprises a retaining plate having perforations therein adapted to allow the hollow projections to pass therethrough, wherein the retaining plate is fastened to the first base by a second fastening means, wherein the membrane is disposed between the first base and the retaining plate.

In another aspect, the present invention provides a method of measuring diffusion of a compound through a membrane comprising:

providing a system according to the present invention;

placing a first fluid composition into at least one cavity in the first base;

placing a second fluid composition comprising a compound into at least one cavity in the second base, wherein the cavities in the first and second bases are in fluid communication through the membrane; and analyzing the compound content of the first fluid composition.

In another aspect, the present invention provides a system, in kit form, for holding a membrane comprising:

a first base having first and second opposed surfaces and having a plurality of hollow projections extending outwardly from the first surface, each hollow projection having a tapered tip with an opening therein and a respective cavity contiguous with the opening disposed within the projection;

a second base having first and second opposed surfaces, the first surface having a plurality of recessed tapered openings therein adapted to engage the plurality of hollow projections, each recessed tapered opening being contiguous with a respective cavity that extends into the second base; and means for fastening the first base to the second base wherein: a) each cavity within a hollow projection extends through the first base and forms an opening at the second surface of the first base; or b) each cavity within the second base extends through the second base and forms an opening at the second surface of the second base; or c) each cavity within a hollow projection extends through the first base and forms an opening at the second surface of the first base, and each cavity within the second base extends through the second base and forms an opening at the second surface of the second base.

In one embodiment, the kit further comprises a retaining plate having perforations therein adapted to allow the hollow projections to pass therethrough, and means for fastening the retaining plate to the second base.

As used herein:

"membrane diffusion" refers to the rate of diffusion of a compound through a membrane.

DETAILED DESCRIPTION

Figure 1:
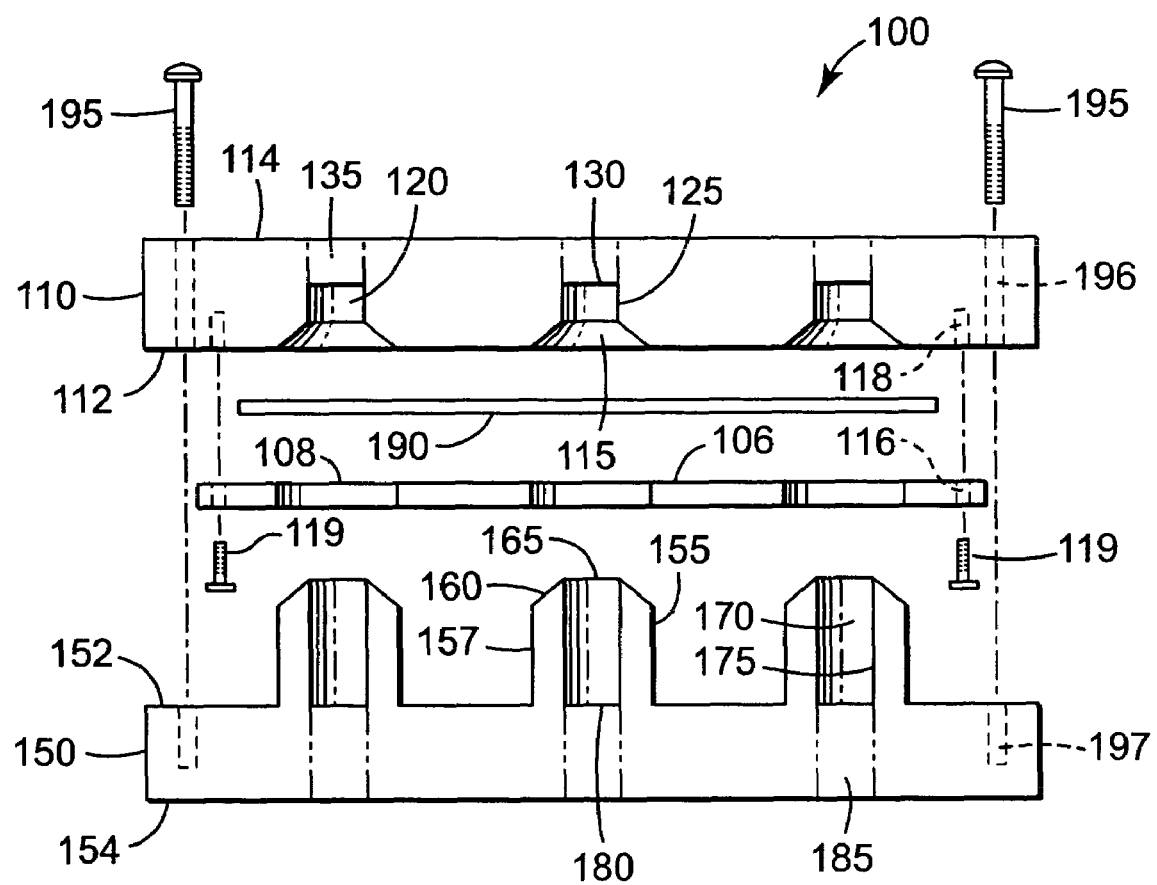
FIG. 1 is a cross-sectional side view of an exemplary system according to one embodiment of the present invention.

Referring to FIG. 1, exemplary system 100 for holding a membrane comprises first base 150 having first and second opposed surfaces 152 and 154, respectively. A plurality of hollow projections 155 extend outwardly from first surface 152, each hollow projection 155 having an outer wall 157 and tapered tip 160 with an opening 165 therein. Each hollow projection 155 has a cavity 170 contiguous with opening 165 disposed therein.

Each cavity 170 has one or more sides 175. In one embodiment, each cavity 170 has a respective bottom 180. Bottoms 180 may be at the same or different depths. In another embodiment, sides 175 extend into first base 150, optionally extending through the first base 150 to second surface 154 to form passages 185.

Second base 110 has first and second opposed surfaces 112 and 114, respectively. First surface 112 has a plurality of recessed tapered openings 115 therein adapted to engage tapered tips 160. Each recessed tapered opening 115 is contiguous with a cavity 120 that extends into second base 110. Each cavity 120 has one or more sides 125. In one embodiment, each cavity 120 has a respective bottom 130. In another embodiment, the sides 125 extend into second base 110, optionally extending through second base 110 to second surface 114 to form passages 135.

In typical use, membrane 190 is positioned between first base 150 and second base 110, and first base 150 and second base 110 are fastened together by a fastening means, shown by screws 195 (which pass through holes 196 and engage threaded holes 197), such that hollow projections 155 engage recessed tapered openings 115 with membrane 190 fixed therebetween.

In one embodiment, system 100 further comprises optional retaining plate 106, which has perforations 108 therethrough adapted to allow at least a portion of each hollow projection 155 (e.g., a portion of tip 160) to pass therethrough. For example, perforations 108 may be of sufficient spacing and shape to permit hollow projections 155 to simultaneously pass through perforations 108. Alternatively, the perforations 108 may be of sufficient spacing and shape to permit, for example, only a portion of tapered tips 160 to extend through perforations 108, but not allow hollow projections 155 to simultaneously pass through perforations 108. Retaining plate 106 is fastened to second base 110 by a second fastening means shown by screws 119, which pass through holes 116 in retaining plate 106 and engage threaded holes 118 in second base 110.

In general, the optional retaining plate may be positioned on either side of the membrane, and may be fastened to either the first base or the second base. The retaining plate may assist in maintaining membrane shape and integrity, and also allows the first base to be unfastened from the second base-membrane-retaining plate subassembly and refastened (e.g., to facilitate analysis of liquids contains in cavities of the first base) without changes in membrane position and/or the need to refill cavities in the second base with liquid.

Figure 2:
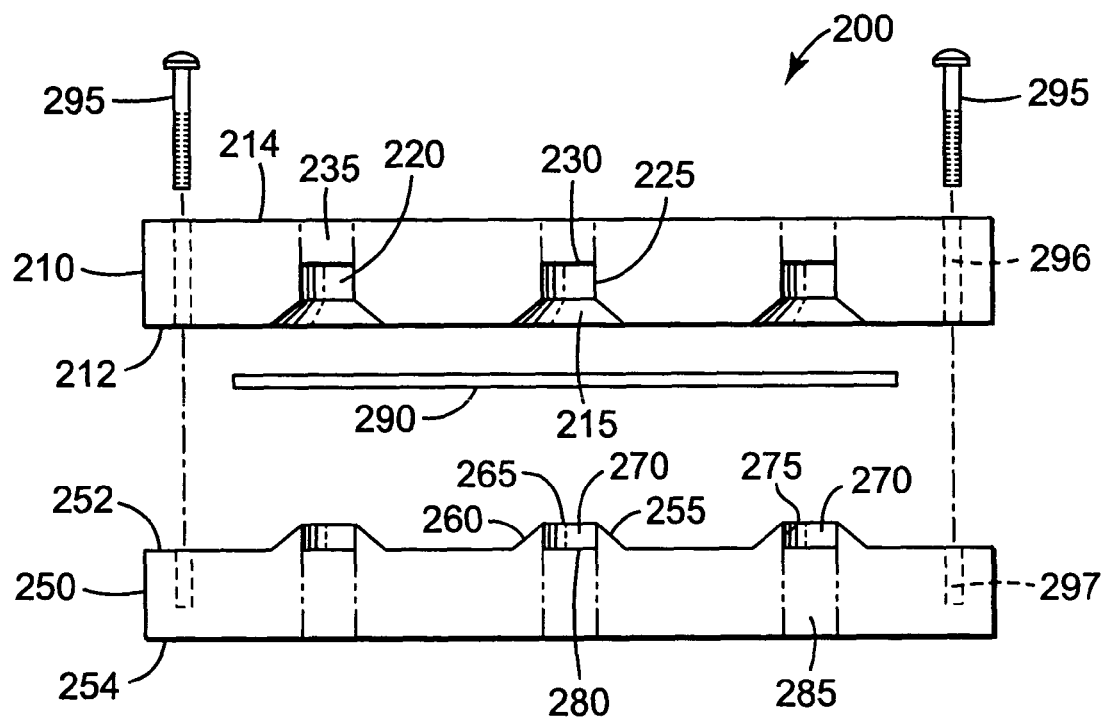
FIG. 2 is a cross-sectional side view of an exemplary system according to one embodiment of the present invention.

Referring now to FIG. 2, exemplary system 200 comprises first base 250, having first and second opposed surfaces 252 and 254, respectively. A plurality of hollow projections 255 consisting of tapered tips 260 extend outwardly from first surface 252, each tapered tip 260 having an opening 265 therein. Each tapered tip 260 has a cavity 270 contiguous with opening 265 disposed therein.

Each cavity 270 has one or more sides 275. In one embodiment, each cavity 270 has a respective bottom 280. In another embodiment, the sides 275 extend into first base 250, and may even extend through the first base to second surface 254, thereby forming passages 285.

Second base 210 has first and second opposed surfaces 212 and 214, respectively. First surface 212 has a plurality of recessed tapered openings 215 therein adapted to engage tapered tips 260. Each recessed tapered opening 215 is contiguous with a cavity 220 that extends into second base 210. Each cavity 220 has one or more sides 225. In one embodiment, each cavity 220 has a respective bottom 230. In another embodiment, sides 225 extend into second base 210, and may even extend through second base 210 to second surface 214, thereby forming passages 235.

In typical use, membrane 290 is positioned between first base 250 and second base 210, and first base 250 and second base 210 are fastened together by a fastening means, shown by screws 295 (which pass through holes 296 and engage threaded holes 297).

The first and second bases and the retaining plate may be made of any material, including, for example, metal, glass, ceramic, plastic, and combinations thereof, and may be opaque, transparent and/or translucent. The first and second bases may have any shape (e.g., a block or plate) and/or thickness.

Systems according to the present invention may have any number of hollow projections greater than one (e.g., 2, 12, 24, 32, 64, 96, or even as many as 256 hollow projections or more). Hollow projections may individually have any shape including, for example, cylindrical, prismatic, or conical shapes. Hollow projections may have any, typically about equal, height relative to the base. Each hollow projection has a tapered tip, which may be of any shape as long as it generally narrows toward the outermost end of the tapered tip.

Tapered tips may have any cross-sectional profile. Openings in the tapered tips may have any shape, such as for example, circular or polygonal. The area of the openings may be of any size, for example, greater than about 0.01, 0.05, 0.1, 0.5, or even about 1 square centimeter, or even more.

Cavities in the hollow projections, and/or the first and second bases may have any shape and/or depth, and their bottoms may have any shape (e.g., flat and/or rounded).

Figure 3:
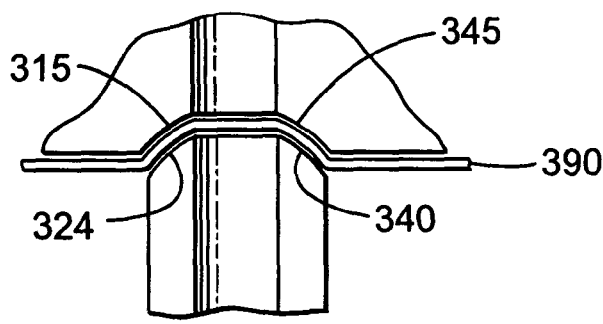
FIG. 3 is a cross-sectional side view showing an exemplary engaged tapered projection and tapered recess.
Figure 4:
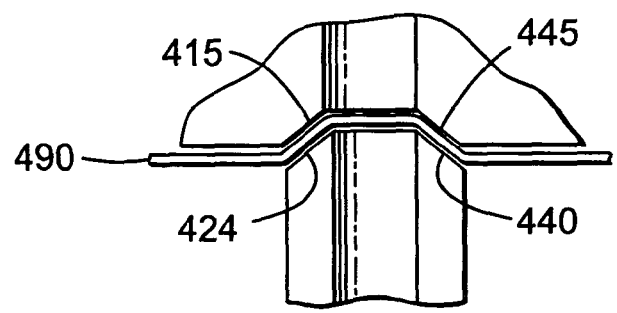
FIG. 4 is a cross-sectional side view showing an exemplary engaged tapered projection and tapered recess.

Referring now to FIG. 3, the cross-sectional profile of one or more tapered tips 324 may comprise an arcuate portion 340. Referring now to FIG. 4, the cross-sectional profile of one or more tapered tips 424 may comprise a beveled portion 440. In some embodiments, the cross-sectional profile of the tip comprises a beveled portion and an arcuate portion.

Similarly, recessed tapered openings may individually have any shape, but are typically chosen to have a shape that is complementary to tapered tips that they engage, in order that a tight seal may be formed with a membrane when the tip and recessed tapered opening are engaged with a membrane therebetween. Thus, as shown in FIG. 3, the cross-sectional profile of recessed tapered openings 315 may comprise an arcuate portion 345. Similarly, as shown in FIG. 4, the cross-sectional profile of recessed tapered openings 415 may comprise a beveled portion 445. In some embodiments, the cross-sectional profile of the tip may comprise both a beveled portion and an arcuate portion.

As shown in FIGS. 3 and 4, the tapered tips are adapted to engage the recessed tapered openings fixing membrane 390 or 490, respectively, therebetween.

Typically, the precise shape of the recessed tapered openings and the tapered tips is not important, however to prevent perforation of the membrane when assembling systems according to the present invention, the depth of the recessed tapered openings may be limited to less than about 1, 0.5, 0.3, 0.2, or even less than about 0.1 centimeters, and the average angle of the taper may be limited to less than about 45, 30, or even less than about 20 degrees from the surrounding surface.

Fastening means utilized in the present invention (e.g., means for fastening the first and second bases, means for fastening the retaining plate to the second base, means for fastening the covering means to the second base, and/or means for fastening the cover plate to the first base) may be removable or non-removable. Useful fastening means include mechanical, adhesive, and attractive (e.g., magnetic, gravitational) means. Removable fastening means include, for example, screws, removable adhesives, clamps, staples, clips, nails, pins, hook and loop fasteners, weights, mushroom-type mechanical fasteners, snaps and combinations thereof. Non-removable fastening means include, for example, non-removable adhesives, rivets, welds, locking snap connectors, soldered joints, and combinations thereof.

During positioning the membrane between the first base and the second base the membrane is typically smoothed (e.g., manually) to remove wrinkles prior to fixing it in place (e.g., by fastening a retaining plate to a base or by fastening the two bases together).

Suitable membranes are typically thin soft pliable sheets including, for example, synthetic polymer membranes (e.g., cellulose acetate sheets, polymeric membranes containing ethyl cellulose, phospholipids, cholesterol, and mineral oil, polyurethane polymers containing poly(ethylene glycol) block segments, synthetic zeolites incorporated into poly(styrene), silicone rubbers, laminated polymer sheets containing alternating hydrophilic and hydrophobic sheets, filter papers or membranes loaded with organic liquids, and cultured cell membranes); hairless mouse skin; snake skin; pig skin; and cadaver skin. Further details concerning suitable synthetic membranes that are useful as substitutes for mammalian skin in permeation testing are described by, for example, Houk et al. in "Membrane Models for Skin Penetration Studies", Chemical Reviews (1988), vol. 88(3), pages 455-472, and by Hatanaka et al. in "Prediction of Skin Permeability of Drugs. II. Development of Composite Membrane as a Skin Alternative", International Journal of Pharmaceutics (1992), vol. 79, pages 21-28.

Systems according to the present invention may be used in any orientation. However, to facilitate assembly it may be useful to horizontally orient the bases while filling cavities therein and assembling the system.

In typical use, one of the first or second bases is used as a formulation plate that contains a plurality of compositions comprising one or more compounds (e.g., pharmaceuticals, excipients, dyes, chemical reagents and mixtures thereof, nutriceuticals, vitamins, cosmoceuticals) to be evaluated and the other as a receiving plate. For example, the second base may be the formulation plate, and the first base may be the receiving plate, or vice versa.

Figure 5:
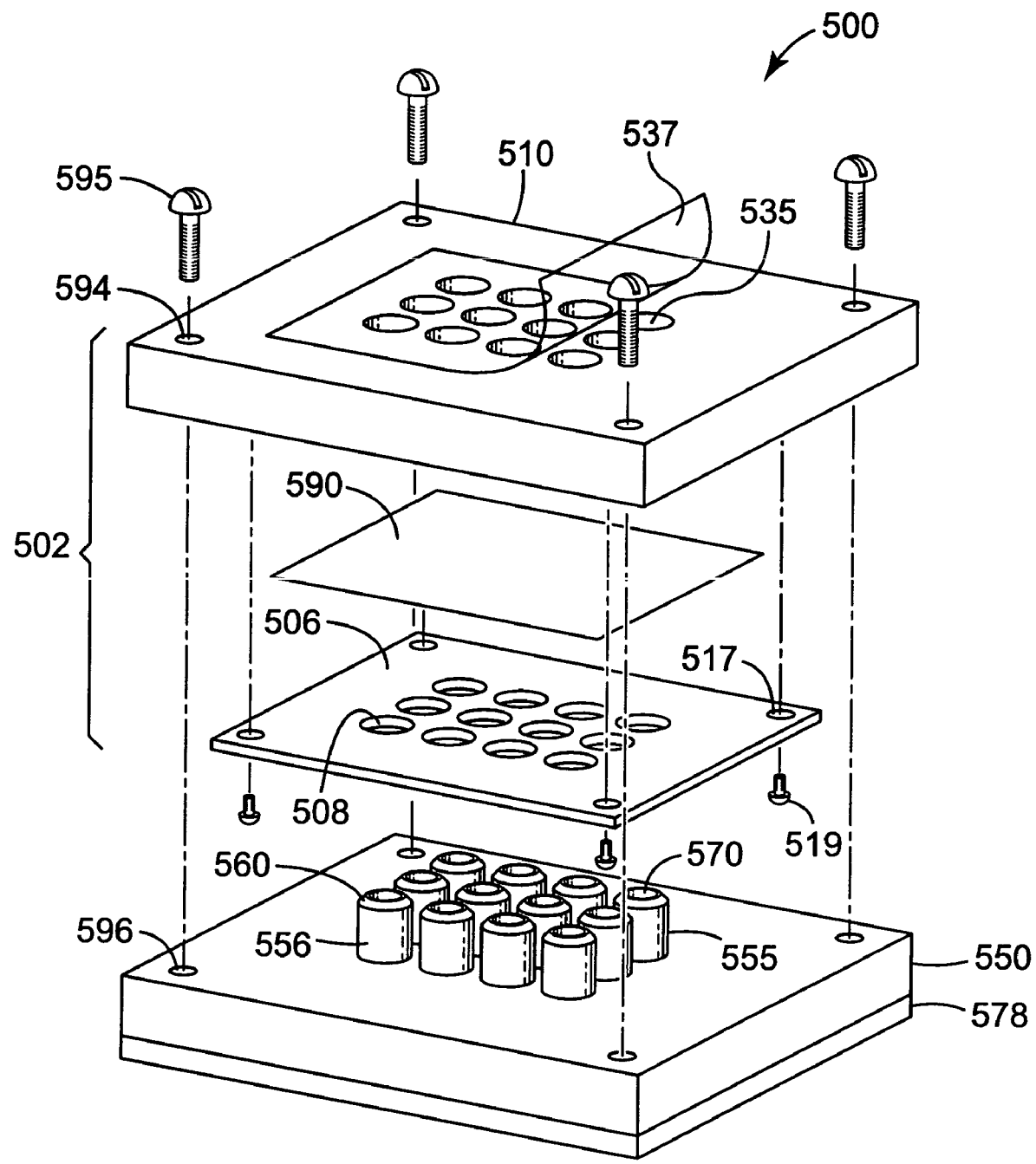
FIG. 5 is an exploded perspective view of one exemplary embodiment of the present invention.

In one exemplary system 500, shown in FIG. 5, membrane 590 is positioned against formulation plate 510 thereby covering recessed tapered openings 515 (not shown) in formulation plate 510. Retaining plate 506, having perforations 508 therein, is fastened to formulation plate 510 by means of screws 519, which pass through holes 517 in retaining plate 506 and engage threaded holes 518 (not shown) in formulation plate 510, thereby forming subassembly 502. Subassembly 502 is fastened to receiving plate 550 by screws 595 that pass through holes 594 in formulation plate 510 and engage threaded holes 596 in receiving plate 550. Advantageously, in this embodiment subassembly 502 can be repeatedly fastened to, and unfastened from, receiving plate 550 without having to handle membrane 590.

Membrane 590 is typically smoothed (e.g., manually) to remove wrinkles prior to fastening retaining plate 506 to formulation plate 510. Compositions to be evaluated (not shown) are placed into passages 535 in formulation plate 510, which are covered by tape 537 to facilitate handling and/or to reduce evaporation. Tape 537 may be replaced by other covering means such as, for example, a cover plate.

Cavities 570 in hollow projections 555 of receiving plate 550 are filled with a receiving liquid (e.g., serum or a synthetic version thereof, not shown). To help avoid the formation of air gaps during assembly that may, for example, lead to erroneous membrane diffusion rates, cavities 570 may be overfilled with receiving liquid to the maximum point permitted by the surface tension of the receiving liquid. Formulation plate 510 and receiving plate 550 are then fastened together such that tapered tips 560 engage recessed tapered openings 515, fixing membrane 590 therebetween. During this process, membrane 590 is typically stretched across openings 570 in tapered tips 560 and compressed between tapered tips 560 and recessed tapered openings 515, thereby ensuring a tight seal and reducing, or more typically, eliminating the possibility of crosstalk between adjacent cells. Elongated body portions 556 of hollow projections 555 further help to prevent crosstalk by allowing any liquids that leak out of one cell to harmlessly drain away by gravity, for example, when the system is oriented with hollow projections 555 extending vertically upward.

Systems according to the present invention may further comprise one or more covering means, for example, as shown in FIG. 5 by tape 537 and/or cover plate 578, that is present if cavities 570 extend through receiving plate 550. Suitable covering means include, for example, films, sealing mats, plates, stoppers, and combinations thereof. The covering means may be, for example, a unitary covering means (e.g., a film, tape, or cover plate) or a non-unitary covering means (e.g., a plurality of films, tapes, stoppers, rubber septa, or a combination thereof).

Figure 6:
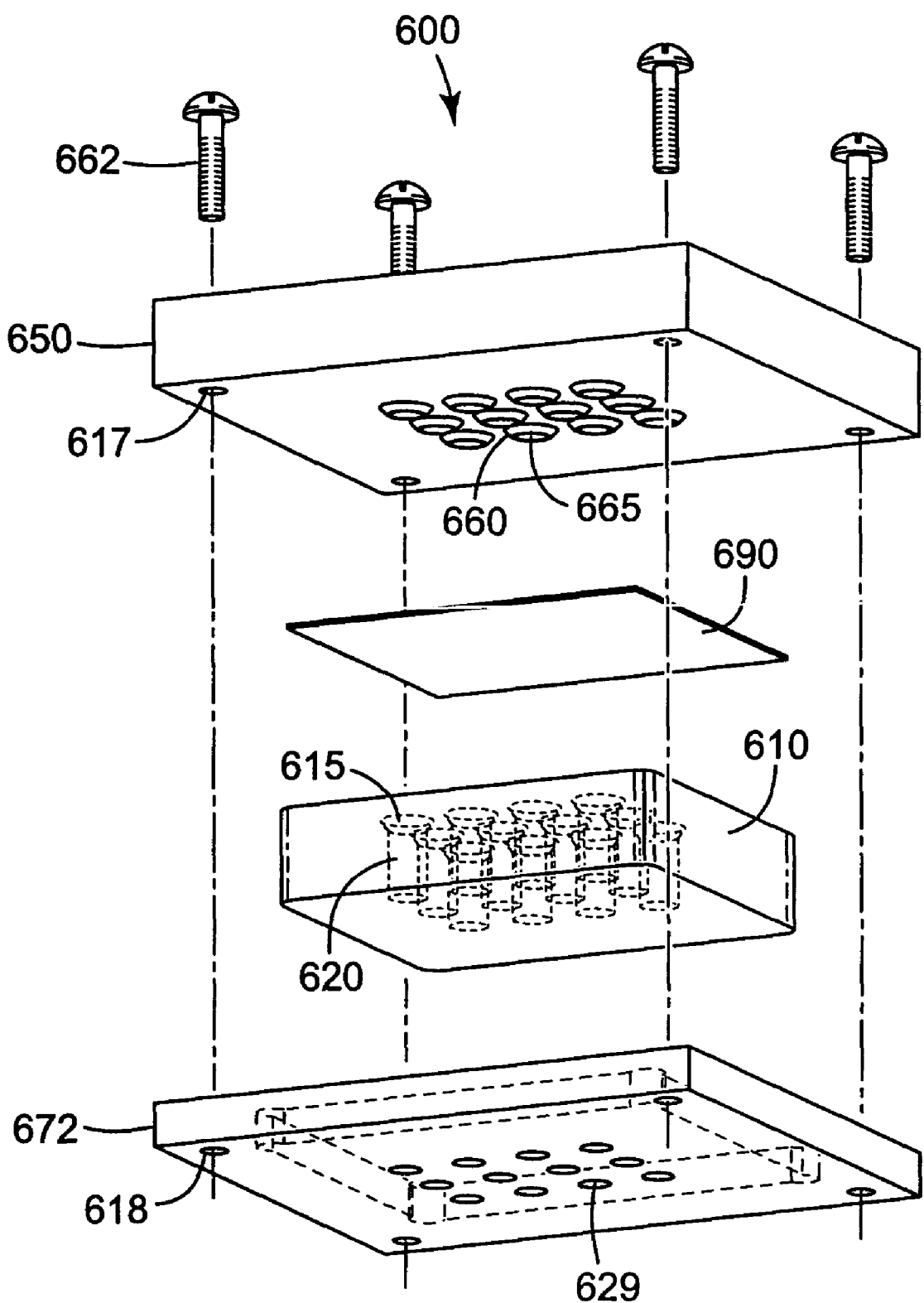
FIG. 6 is an exploded perspective view of one exemplary embodiment of the present invention.

In another exemplary system 600, shown in FIG. 6, formulation plate 650 has hollow projections that consist of tapered tips 660. Passages 685 (not shown) extend through formulation plate 650 and form openings 665 in tapered tips 660. Receiving plate 610 has recessed tapered openings 615 therein adapted to engage tapered tips 660. Cavities 620 are contiguous with recessed tapered openings 615. Receiving plate 610 is fastened to formulation plate 650 by retaining bracket 672 and screws 662 that pass through holes 617 and engage threaded holes 618, such that tapered tips 660 engage recessed tapered openings 615, fixing membrane 690 therebetween. Receiving plate 610 is optically transparent and retaining bracket 672 has perforations 629 therethrough of appropriate spacing and alignment to permit optical detection of the contents of cavities 620.

Optical detection methods include, for example, visual inspection, spectroscopic methods, optical scanners, and videographic and photographic methods (including digital photographic methods).

Systems according to the present invention may be used in conjunction with various known collection, automated dispensing equipment, and/or autosampling equipment. Examples of such equipment include liquid handling robots, for example, such as those commercially available from Gilson, Inc., Middleton, Wis. and well plates (e.g., having 24, 96, or 384 wells) such as, for example, those available from Weidmann Plastics Technology AG, Rapperswil, Switzerland.

Systems according to the present invention may be provided in assembled or kit form (i.e., unassembled or partially assembled), with or without a membrane.

Various unforeseeable modifications and alterations of this invention may be made by those skilled in the art without departing from the scope and spirit of this invention, and it should be understood that this invention is not to be unduly limited to the illustrative embodiments set forth herein.

What is claimed is:

1. A system for measuring diffusion of a compound across a membrane comprising:
    a first base having first and second opposed surfaces and having a plurality of hollow projections extending outwardly from the first surface, each hollow projection having a tapered tip with an opening therein and a respective cavity contiguous with the opening disposed within the projection;
    a second base having first and second opposed surfaces, the first surface of the second base having a plurality of recessed tapered openings therein adapted to engage the plurality of hollow projections, each recessed tapered opening being contiguous with a respective cavity that extends into the second base;
    a membrane contacting the recessed tapered openings and the tips of the hollow projections, wherein the first base is fastened to the second base by a first fastening means, and wherein: a) each cavity within a hollow projection extends through the first base and forms an opening at the second surface of the first base; or b) each cavity within the second base extends through the second base and forms an opening at the second surface of the second base; or c) each cavity within a hollow projection extends through the first base and forms an opening at the second surface of the first base, and each cavity within the second base extends through the second base and forms an opening at the second surface of the second base; and
    a retaining plate having perforations therein adapted to allow the hollow projections to pass therethrough, wherein the retaining plate is fastened to the second base by a second fastening means, wherein the membrane is disposed between the second base and the retaining plate.

2. The system of claim 1, wherein at least a portion of at least the first or second base is transparent or translucent.

3. The system of claim 1, wherein the first fastening means is a removable means.

4. The system of claim 1, wherein each cavity within a hollow projection, extends through the first base and forms an opening at the second surface of the first base.

5. The system of claim 4, further comprising a first covering means fastened to the second surface of the second base.

6. The system of claim 1, wherein the cavity in each hollow projection extends into the first base.

7. The system of claim 1, wherein the cavity in each hollow projection extends through the second base and forms an opening at the second major surface of the second base.

8. The system of claim 1, further comprising a cover plate fastened to the second surface of the first base.

9. The system of claim 8, wherein at least a portion of the cover plate is transparent or translucent.

10. The system of claim 1, wherein the first and second surfaces of at least one of the first and second bases are major surfaces.

11. The system of claim 1, wherein at least one of the first and second bases comprises a plate.

12. The system of claim 1, wherein each tapered tip has a cross-sectional profile that comprises a least one of an arcuate portion or a beveled portion.

13. The system of claim 1, wherein each recessed tapered opening huh a cross-sectional profile that comprises at least one of an arcuate portion or a beveled portion.

14. The system of claim 1, wherein the projections further comprise a body portion having at least one wall.

15. The system of claim 14, wherein the body portion is cylindrical.

16. The system of claim 1, wherein the membrane comprises a synthetic polymer.

17. The system of claim 1, wherein the membrane comprises animal tissue.

18. The system of claim 1, wherein the membrane comprises skin.

19. The system of claim 1, wherein the second fastening means is removable.

20. A system, in kit form, for holding a membrane comprising:
    a first base having first and second opposed surfaces and having a plurality of hollow projections extending outwardly from the first surface, each hollow projection having a tapered tip with an opening therein and a respective cavity contiguous with the opening disposed within the projection;
    a second base having first and second opposed surfaces, the first surface having a plurality of recessed tapered openings therein adapted to engage the plurality of hollow projections, each recessed tapered opening being contiguous with a respective cavity that extends into the second base;
    means for fastening the first base to the second base wherein: a) each cavity within a hollow projection extends through the first base and forms an opening at the second surface of the first base; or b) each cavity within the second base extends through the second base and forms an opening at the second surface of the second base; or c) each cavity within a hollow projection extends through the first base and forms an opening at the second surface of the first base, and each cavity within the second base extends through the second base arm forms an opening at the second surface of the second base;
    a retaining plate having perforations therein adapted to allow the hollow projections to pass therethrough; and
    means for fastening the retaining plate to the second base.

21. The system of claim 20, wherein each cavity within a hollow projection extends through the first base and forms an opening at the second surface of the first base.

22. The system of claim 20, wherein each cavity within the second base extends through the second base and forms an opening at the second surface of the second base.

* * * * *

UNITED STATES PATENT AND TRADEMARK OFFICE
CERTIFICATE OF CORRECTION

PATENT NO. : 7,635,452 B2  Page 1 of 1
APPLICATION NO. : 10/669276
DATED : December 22, 2009
INVENTOR(S) : Roscoe et al.

It is certified that error appears in the above-identified patent and that said Letters Patent is hereby corrected as shown below:

Column 7

Line 52; Claim 4, delete "projection," and insert -- projection --, therefor.

Column 8

Line 9; Claim 12, delete "a least" and insert -- at least --, therefor.

Column 8

Line 12; Claim 13, delete "huh" and insert -- has --, therefor.

Column 8

Line 50; Claim 20, delete "arm forms" and insert -- and forms --, therefor.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,635,452 B2
APPLICATION NO. : 10/669276
DATED : December 22, 2009
INVENTOR(S) : Roscoe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1675 days.

Signed and Sealed this

Ninth Day of November, 2010

David J. Kappos
*Director of the United States Patent and Trademark Office*